(12) United States Patent
Gill (10) Patent No.: US 6,609,020 B2
(45) Date of Patent: Aug. 19, 2003

(54) NEUROSURGICAL GUIDE DEVICE

(76) Inventor: Steven Gill, Old Rectory Church Road, Old Bury on Severn (GB), BS351QG (*) Notice: Subject to any disclaimer, the term of this patent is extended or adjusted under 35 U.S.C. 154(b) by 108 days.

(21) Appl. No.: 09/728,696

(22) Filed: Dec. 1, 2000

(65) Prior Publication Data

US 2001/0003156 A1 Jun. 7, 2001

(30) Foreign Application Priority Data

Dec. 1, 1999 (GB) .............................. 9928248

(51) Int. Cl.⁷ .............................. A61B 5/05; A61F 7/00
(52) U.S. Cl. .................. 600/423; 607/112; 607/116
(58) Field of Search ................................ 600/378, 421, 600/423, 429, 433, 434, 417, 382, 383; 607/112, 113, 116; 606/32, 129, 130; 604/164.11, 175; 128/898, 899, DIG. 26

(56) References Cited

U.S. PATENT DOCUMENTS

| | | | | |
|---|---|---|---|---|
| 3,333,588 A | * | 8/1967 | Schulte | 604/175 |
| 4,245,645 A | * | 1/1981 | Arseneault et al. | 600/378 |
| 4,328,813 A | * | 5/1982 | Ray | 607/139 |
| 4,840,617 A | | 6/1989 | Osterholm | |
| 4,903,707 A | * | 2/1990 | Knute et al. | 600/561 |
| 5,116,345 A | | 5/1992 | Jewell et al. | |
| 5,180,365 A | | 1/1993 | Ensminger et al. | |
| 5,464,446 A | * | 11/1995 | Dreessen et al. | 604/175 |
| 5,713,858 A | | 2/1998 | Heruth et al. | |
| 5,843,150 A | * | 12/1998 | Dreessen et al. | 128/898 |
| 5,927,277 A | * | 7/1999 | Baudino et al. | 600/386 |
| 5,928,144 A | * | 7/1999 | Real | 600/372 |
| 5,954,687 A | * | 9/1999 | Baudino | 604/174 |
| 6,006,124 A | * | 12/1999 | Fischell et al. | 600/378 |

* cited by examiner

Primary Examiner—Sang Paik
(74) Attorney, Agent, or Firm—Pearne & Gordon LLP (57) ABSTRACT

The present invention relates to a neurosurgical guide device for use in neurosurgery. The device is particularly useful in stereotactically targeted surgical treatment of abnormalities of brain function. The neurosurgical guide device comprising a tube for insertion into a brain of a patient to a vicinity of a desired target, wherein the tube has a head attached to one end thereof, and whereby an instrument can be introduced through the opening and passed along the bore from a proximal end to a distal end thereof.

19 Claims, 5 Drawing Sheets

NEUROSURGICAL GUIDE DEVICE

The present invention relates to a neurosurgical guide device for use in neurosurgery. The device is particularly useful in stereotactically targeted surgical treatment of abnormalities of brain function, including abnormalities of movement such as Parkinson's disease, chorea, tremor, multiple sclerosis and cerebral palsy; abnormalities of the mind including depression, obsessive compulsive states and Alzheimer's disease; chronic pain syndromes and epilepsy. The device can also be used in the targeted treatment of brain tumours.

In order to perform neurosurgery, the surgeon needs, in the first instance to localise the desired target. This is conventionally achieved by fixing a stereotactic reference frame to the patient's head, which can be seen on the diagnostic images and from which measurements can be made. The stereotactic frame then acts as a platform from which an instrument is guided to a desired target using a stereoguide that is set to measure co-ordinates. Once an instrument is guided to the desired target, treatment can begin. For example, where the instrument is an electrode, the target area can be functionally neutralised by controlled heating at the electrode tip (radio-frequency lesioning), or by delivering high frequency electrical stimulation to the target through a chronically implanted deep brain stimulation (DBS) electrode.

Other instruments that can be used include catheters, probes for monitoring brain metabolic or electrical activity. In recent years fetal cells have been implanted into the brains of patients with Parkinson's disease using stereotactic techniques and function has been successfully restored. Drugs or tropic substances (such as nerve growth factor) may also be delivered at a targeted intraparenchymal site. Such drugs and tropic substances will modulate and may restore brain function when delivered stereotactically using catheters targeted to the desired site.

A number of difficulties are encountered in such neurosurgical procedures. Including sub-optimal placement of the instrument which may lead to significant morbidity or failure of the treatment. Sub-optimal placement may result from brain shift during the operative procedure, deflection of the instrument as it passes through the brain substance to the desired target or may result from miscalculation by the surgeon.

In order to confirm accurate target localisation preoperatively, the surgeon typically guides a microelectrode to the target to record characteristic neural firing patterns and/or pass a stimulating electrode to the target site to locally depolarised neural tissue and create a reversible functional lesion. These procedures are generally performed when the patient is awake so that functional change can be observed. A common problem with these techniques is that the passage of an electrode into or through the target will cause a mechanical lesion which will disrupt neural firing at the target site and may cause a fictional improvement. In view of this, the surgeon can lose the necessary teed-back for accurately placing the electrode. This effect is termed "impact effect".

If the surgeon does successfully identify the target site with the electrode, then the process of removing the electrode and replacing it with an instrument (which may be a lesioning or DBS electrode), may lead to an error in the positioning of the end of the instrument due to brain shift. The instrument may create a new tract through the brain, follow the tract of another test tract to a sub-optimal target site, or sinking of the brain due to loss of the cerebro spinal fluid (CSF) may result in placement of the instrument above the optimal target site.

Furthermore, if the surgical treatment is a thermal lesion, the surrounding tissue becomes acutely swollen. The swollen tissue will be functionally inactivated and so an under-sized lesion with surrounding swelling that is confined to the target will give a good functional result during the post operative period. However, the benefits will fall off as the swelling settles and the surgery may need to be repeated. Typically, up to 20% of patients require repeated surgery at the same target site.

Brain tumours may be targeted for treatment by the interstitial implantation of radio-isotopes into the tumour, or the implantation of a catheter into the tumour to deliver anti-tumour agents. As with functional neurosurgery, difficulties with established techniques include per-operative brain shift which may result in radiation or the anti-tumour agents being delivered to a sub-optimal site and damaging normal tissue.

When treating a tumour with interstitial radiotherapy an "after loading" method is typically employed in which a catheter is stereotactically inserted to the target and brought out through the scalp where it is secured using a fixation sleeve which is attached to the scalp. Radionuclide seeds such as Iodine 125 are placed in an inner catheter and this is then "after loaded" into the fixed catheter for a treatment period of days or weeks. Because this system is externalised, there remains a significant risk of infection tracking into the brain and causing morbidity. Furthermore, because the catheter is secured to the scalp, there can be some movement which may lead to delivery to a sub-optimal site.

U.S. Pat. No. 5,954,687 discloses a burr hole ring for use with a catheter, wherein the burr hole ring engages the skull. The burr bole ring is sealed by a septum and does not allow the insertion of medical instruments into the brain along a specific trajectory.

U.S. Pat. No. 4,840,617 discloses a catheterization apparatus for delivering oxygenating nutrients to or from the cerebral-spinal fluid of a patient.

U.S. Pat. No. 5,713,858 discloses a permanently implanted catheter. The catheter is sealed via a septum and does not enable insertion of instruments along a desired trajectory.

U.S. Pat. No. 5,116,345 discloses an apparatus for implanting an instrument into a brain. The device requires the positioning a temporary skull bolt that protrudes above the scalp of a patient leading to problems with the stability of the device and possible infection. The device does not allow repeated access to a desired target site over a prolonged period of time.

U.S. Pat. No. 5,180,365 discloses an implantable infusion device which cannot be used for inserting instruments along a defined trajectory.

U.S. Pat. No. 5,927,277 discloses an apparatus for securing medical devices within a cranial burr hole. The device does not allow the insertion of an instrument along a defined trajectory to a desired target site.

The present invention provides a neurosurgical guide device comprising a tube for insertion into a brain of a patient to the vicinity of a desired target, wherein the tube has a head attached to one end thereof, the head having a passageway therethrough in communication with the bore of the tube and which terminates in an opening on the outer surface of the head, and having one or more formations on its external surface for securing the device in a hole formed in a skull of the patient, whereby an instrument can be introduced through the opening and passed along the bore from a proximal end to a distal end thereof.

The neurosurgical guide device of the present invention can be used in functional neurosurgery or other stereotactic surgical procedures wherein an instrument has to be inserted to a specific target site in the brain of a patient.

The guide device of the present invention is sized and configured for receiving a neurosurgical instrument. The term "a neurosurgical instrument" or "instrument" as used herein refers to any instrument which can be used in a neurosurgical procedure. Preferably the instrument is a deep brain surgical instrument. It is particularly preferred that the instrument is an electrode such as a lesioning or stimulating electrode, a catheter, or a probe such as a microdialysis probe for the metabolic state, an electrode for measuring the electrical state or a pressure transducer.

The head of the guide device of the present invention preferably has a greater diameter than that of the tube allowing the tube to be easily inserted in the hole formed in the skull while still to allow the head to be fixed within the hole.

The tube of the device of the present invention is of a length sufficient to extend from the head when fixed in the hole formed in the skull to the vicinity of the target site. Preferably the tube is at least 2 cm in length, more preferably at least 4 cm in length and most preferably at least 7 cm in length The term "vicinity of the target site" means within 2 cm of the target site, more preferably within 1 cm of the target site and most preferably within 5 mm of the target site.

The head is secured within the hole formed in the skull via one or more formations on its external surface. These formations can be one or more protrusions or recesses formed in the head resulting in the fixation of the head to the skull of a patient. Preferably the one or more formations comprise one or more shoulders formed on the external surface of the head. It is further provide that the one or more formations are a thread formed on the external surface of the head.

The head can be attached directly to the skull by having the formations formed on the external surface of the head in direct contact with the sides of the hole formed in the skull. Alternatively, the head can be indirectly attached to the skull via a filler. In this case, the formations of the external surface of the head are in contact with a filler present within the hole formed in the skull. Preferably, the filler comprises an acrylic cement. Suitable acrylic cements are well known to those skilled in the art.

In a preferred embodiment of the present invention, the guide device has a head which comprises a slot which extends laterally of the longitudinal axis of the bore from the passageway to an outer surface of the head, for receiving, in use, a protruding end of an instrument located in the device, The slot is formed in the head to enable the protruding end of an instrument to be positioned laterally from the longitudinal axis of the bore by positioning the protruding end of the instrument in the slot. The protruding end of the instrument can then be fixed to the surface of the patient's skull with a clamp such as a small bridge shaped plate and screws. By having the protruding end of the instrument fixed to the patient's skull, there is less chance of the instrument moving within the guide device.

Preferably the passageway from the bore to the slot formed in the head is radiussed in order to prevent any kinking of the instrument inserted into the guide device.

It is further preferred that the length of the path from the distal end of the bore to the opening of the head is substantially the same as the length of the path from the distal end of the bore to the outer surface end of the slot formed on the head. By insuring that these path lengths are substantially identical, on moving the proximal end of the instrument from the opening to the slot, the length of instrument inserted into the device will remain the same.

The term "substantially identical" as used herein means that the lengths of the paths differ by less than 1 mm, preferably less than 0.5 mm.

It is particularly preferred that the head of the device comprises a domed surface on which the opening of the head and the outer surface end of the slot are disposed. It is further preferred that the domed surface forms a constant radius curve ensuring that the lengths of the paths referred to above are substantially the same length.

The guide device of the present invention is secured in a hole formed in the skull, and will preferably follow the trajectory of the hole formed in the skull leading to the desired target site. Furthermore, once the guide device is in position, it will enable repeated access to the desired site as the guide tube is stably fixed in position. Furthermore, as a slot is preferably provided on the head of the device, the protruding end of an instrument inserted into the device can be located in the slot.

Preferably the guide device is constructed from a suitable plastics material. It is preferred that that plastics material is sufficiently rigid so that there is substantially no movements of the device once it is inserted into a hole formed in the skull of a patient. Suitable plastics materials are well known to those skilled in the art. It is also desirable that the plastics material is bio-compatible. Suitable bio-compatible materials are also well known to those skilled in the art.

The present invention also provides a method of positioning an instrument at a desired target in the brain of a patient, comprising:

(a) drilling a hole in the skull of the patient along a desired trajectory;

(b) inserting the device of the present invention into the hole along the desired trajectory and securing the head in the hole, and (c) inserting the instrument through the opening and passing the instrument along the bore so that the instrument is positioned at the desired target.

Preferably the method of the present invention comprises inserting the guide device of the present invention along a guide rod which is inserted into the hole. The guide rod can be any rigid rod along which the device can be moved.

Preferably, the guide rod can be introduced into the brain using a conventional stereoguide (e.g. the Leksell stereoguide, Elekta Instruments AB). The stereoguide generally contains a carriage which holds a guide block split longitudinally along its length and having a central longitudinal bore. The guide device of the present invention is held in the bore of the guide block and the guide rod is passed through the guide device to the desired target along the desired trajectory set in the stereoguide. Once the end of the guide rod is at the desired target, the halves of the guide block are separated and the guide device is advanced along the guide rod until it reaches the vicinity of the desired target. The head of the guide device is then secured within the hole formed in the skull. The distance of the datum of the stereoguide to the desired target is known and the distance from the outer surface of the head of the guide device is known. It is therefore possible to determine the distance from the outer surface of the head to the desired target. Accordingly, on removing the guide rod from the guide device it is possible to insert an instrument down the guide device to the desired target as the depth of insertion is known. The insertion of a flexible instrument such as a catheter or implantable electrode is aided by pre-inserting a removable ridged wire.

A radio opaque stylette can be inserted into the guide device in order to determine the exact position of the desired target relative to the guide device. Preferably the distal end of the bore of the guide device is from 1 to 20 mm, more preferably 1 to 10 short of the desired target so that when the instrument is inserted into the guide device, it must protrude from the distal end of the bore by 1 to 20 mm in order to be at the desired target. If the desired target is to the side of the longitudinal axis of the bore, it may be possible to bend the end of the instrument in order to ensure that it comes into contact with the desired target.

It is preferred that the stylette has a cap which seals the opening in the head of the guide device when the stylette is inserted. When the guide device is not in use it is preferred that the stylette is inserted to seal the opening.

It is particularly preferred that the instrument inserted into the guide device has a stop which contacts an outer surface of the head and prevents further insertion of the instrument into the device. The stop therefore serves to ensure that a set length of the instrument is inserted into the guide device. By positioning the stop to the correct position on the instrument, it is possible to ensure that the end of the instrument protruding from the distal end of the bore of the guide device comes into contact with the desired target.

When the guide device of the present invention comprises a slot in the head, it is preferred that the protruding end of an instrument inserted into the guide device is located in the slot. When the instrument has a stop which contacts an outer surface of the skull engaging head and prevents further insertion of the instrument into the device, it is preferred that the stop is kept in contact with the outer surface of the enlarged head when the protruding end of the instrument is located in the slot. By ensuring that the stop remains in contact with the outer surface of the head, the length of the instrument inserted into the guide tube will be the same provided the path length from the distal end of the bore to the opening on the head is the same as the path length from the distal end of the bore to the outer surface end of the slot formed on the head.

The present invention also provides the guide device of the present invention for use in therapy. Preferably, the guide device is provided for use in any neurosurgical therapy such as treatment of abnormalities of movement including Parkinson's disease, chorea, tremor, multiple sclerosis and cerebral palsy, abnormalities of the mind including depression, obsessive compulsive states and Alzheimer's disease; chronic pain syndromes and epilepsy. Neurological therapy also includes the treatment of brain tumours.

The present invention also provides a kit for performing neurosurgery comprising:

(a) the device according to the present invention;
(b) an instrument for insertion into the device;
(c) a drill bit for forming a hole in the skull to receive the device; and
(d) a guide rod for guiding the device into the hole.

It is further preferred that the kit of the present invention comprises a radio opaque stylette for insertion into the device. Preferably the radio opaque stylette comprises a cap which seals the opening of the enlarged head when the stylette is inserted into the guide device.

The guide device has a number of advantageous properties. These properties are discussed below.

The guide device minimises per-operative brain shift. When the localisation of a desired target site has been confirmed with stimulation and/or recording studies using a test electrode, the guide device can be introduced down the test electrode, which acts as a guide rod, to within a few millimeters of the target and the head is securely attached to the hole formed in the skull. When the test electrode is withdrawn, the guide device effectively fixes the brain target and ensures accurate placement of an instrument such as a lesioning or DBS electrode.

The guide device of the present invention allows confirmation of optimal target localisation. In those circumstances where an "impact effect" has occurred following the introduction of a test electrode and the surgeon has lost feed-back on the patient to enable accurate placement of a treatment electrode, then the guide device of the present invention may be inserted down the outside of the test electrode, which acts as a guide rod, to a position just short of the desired target and the head of the guide device fixed within the hole formed in the skull. The test electrode can then be withdrawn and a radio opaque stylette of the desired length inserted down the guide device to the desired target. The location of the desired target can now be confirmed with radio diagnostic imaging. When the "impact effect" has worn off, usually days or weeks later, the patient can be returned to theatre, the stylette withdrawn and stimulation studies repeated to further confirm the desired target location function prior to inserting an instrument into the guide device for treating the patient.

Similarly, in those circumstances in which a patient becomes too fatigued during the operative procedure to co-operate with the simulation studies, or when it is necessary to carry out the functional procedure under general anesthetic (i.e. with children) then a guide tube with an indwelling radio-opaque stylette can be inserted to the desired target and its accurate placement confirmed prior to insertion of an instrument for treating the patient.

As indicated above, the radio opaque stylette is preferably constructed from radio-opaque plastic material and has an external diameter slightly smaller than the internal diameter of the guide device. Preferably, the stylette has a stop which contacts an outer surface of the head and prevents further insertion of the stylette into the device. The stop on the stylette is preferably the cap which seals the opening in the head of the guide device. Preferably the stylette is of a length to extend from the outer surface of the head to the desired target.

The guide device of the present invention facilitates repeated or staged access to the same target. The radio-opaque stylette may be left in situ within the guide device as a permanent marker of the target site. Should there be a decline in the functional benefit achieved following treatment of a target site, for example by lesioning the site, then it is simple for the surgeon to repeat the treatment without the extensive work up and imaging that is usually required in order to identify the target site. Under local anesthesia the scalp wound would be reopened over the indwelling guide device, the stylette withdrawn and a test stimulation electrode advanced to the depth of the desired target site. After confirmation of the target site with stimulation studies, the treatment, for example lesioning, can be repeated, the stylette replaced and the wound closed.

For small functional targets in eloquent areas, such as the subthalamic nucleus (STN), it may be safer to make a small, undersized lesion in the first instance, introduce the guide device and leave a stylette within the bore of the guide device and repeat the lesion at a later date to optimise its size.

The guide device of the present invention facilitates directional lesioning. For some functional targets such as the STN, precise treatment placement, such as lesion placement is critical. The STN is deeply placed and only 3 to 4 millimeters in diameter. To place a 1 millimeter diameter electrode centrally in this structure is technically very demanding as a misplacement by 1 millimeter may result in significant morbidity. Use of the guide device of the present invention containing a radio-opaque stylette bore enables the surgeon to confirm accurate placement prior to treatment. If the stylette is seen to be off centre, then a modified instruments such as a lesioning electrode, capable of treatment laterally from the longitudinal axis of the bore, can be used to optimise the treatment.

It is known that electrodes can be used for directional lesioning which are made of a spring steel with a curve at the end inserted into the guide device. The electrode is held straight within an outer tube while being introduced towards the target in the guide device and is then advanced through the outer tube so that the exposed end of the electrode will extend laterally towards a desired target.

The guide device of the present invention provides a reproducible fixation method for DBS electrodes and allows conversion of a DBS lesion to a permanent thermal lesion.

The guide device of the present invention provides a guide for the accurate placement and fixation of DBS electrodes. Should the electrodes subsequently require repositioning (i.e. due to electrode migration or to accommodate growth if it has been implanted in a child, or replacement due to the development of a fault or electrode factor, then this can easily be achieved. If the surgeon wishes to create a permanent lesion at a target that has until that time been stimulated with a DBS electrode, then again this can easily be achieved by removing the DBS electrode from the guide device and inserting a lesioning electrode to the same depth within the guide device and therefore at the same desired target site.

The guide device of the present invention also facilitates the insertion of fine electrodes or catheters to deeply sited functional targets in eloquent areas. Generally, when passing electrodes or catheters to functional targets that are deeply situated in eloquent areas in the brain, it is preferable that they are the smallest diameter possible so as to minimise trauma. If, however, the electrode or guide rod (down which a catheter is passed) is of a small diameter (for example less than 1 millimeter), then it is more likely to be deflected from its target by resistance in the tissues. This can be overcome by passing an electrode or guide rod of larger diameter (e.g. greater than 1 millimeter) through less eloquent areas of the brain and stopping short of the desired target in the more eloquent area. The guide device of the present invention can be inserted into the tract so formed, again short of the desired target and fixed in position as indicated above. A fine electrode or catheter can now be guided to the desired target through the guide device such that the length emerging from the distal end of the guide device and traversing the eloquent brain tissue will be comparatively short and less likely to deflect from the desired target site.

The guide device of the present invention facilitates placement of catheters to a desired target site. For interstitial delivery of therapeutic agents, such as drugs, tropic factors or neural cell grafts, it may be desirable to place a catheter along the longitudinal axis of a nucleus or neural structure and to deliver the therapeutic agents through multiple side ports in the wall of the catheter. It may not be possible or safe to induce the catheter along this desired axis with a straight trajectory from the skull surface. In these circumstances the implantable guide tube may be inserted through a safe trajectory to one side of the desired target site and the catheter introduced on a support having a curved end. The catheter on the support would be kept straight as it passes through the guide device of the present invention, but as it emerges from the distal end of the bore the support will curve and orientate the end of the catheter along the desired axis. The catheter can then be fixed in position and the support removed. Preferably the support is a radio opaque stylette.

The guide device of the present invention has several advantages when used for targeted interstitial treatment of tumors with radio isotopes (brachytherapy). After stereotactically inserting the guide device into the tumour and fixing the head within the hole formed in the skull, a radio opaque stylette can be inserted Radiological confirmation of the position of the guide device can then be performed prior to initiating treatment. Once it is confirmed that the guide device is at the correct position, a radio isotope seed contained in a sealed catheter of the desired length can be inserted into the guide tube after removing the stylette. Preferably the wound formed obtaining access to the skull will heal thus creating a close system for brachytherapy. This will reduce the likelihood of infection and facilitate the chronic implantation of radio isotopes.

When a sufficient dose has been delivered. The catheter containing the radio isotope seed may be withdrawn and the stylette reinserted. At a later date, or if the tumour reoccurs, the stylette may again be withdrawn and radio isotopes reinserted without the need for extensive retargeting that would otherwise be necessary. The guide device of the present invention also enables the insertion of fine catheters to deeply sited tumours for the delivery of therapeutic agents such as cytotoxic agents or anti-tumour antibodies.

Embodiments of the present invention will now be described by way of example only and with reference to the accompanying drawings in which.

Figure 1:
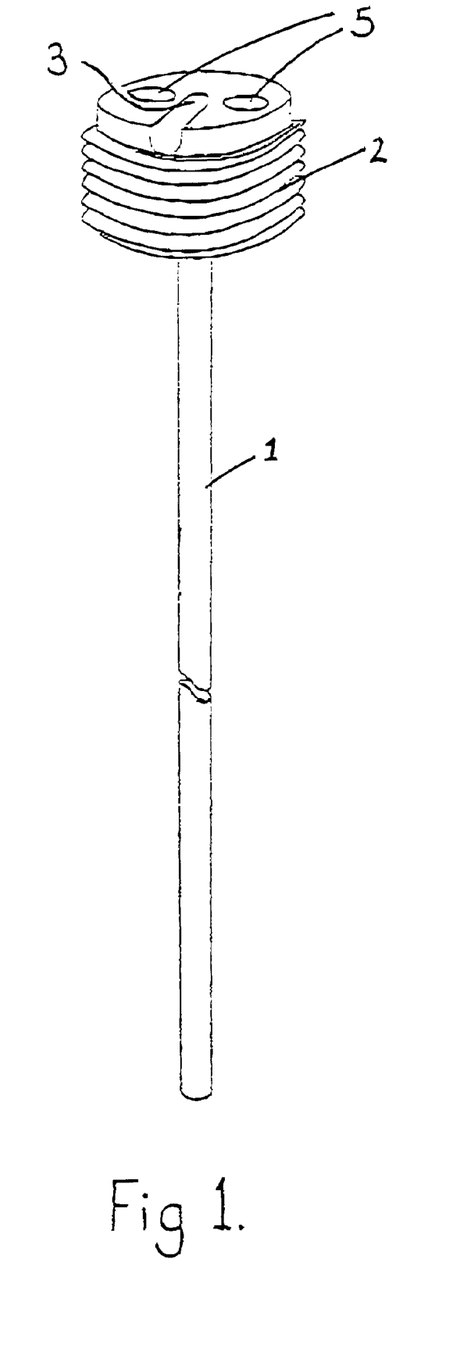
FIG. 1 Shows in perspective a guide device.
Figure 2:
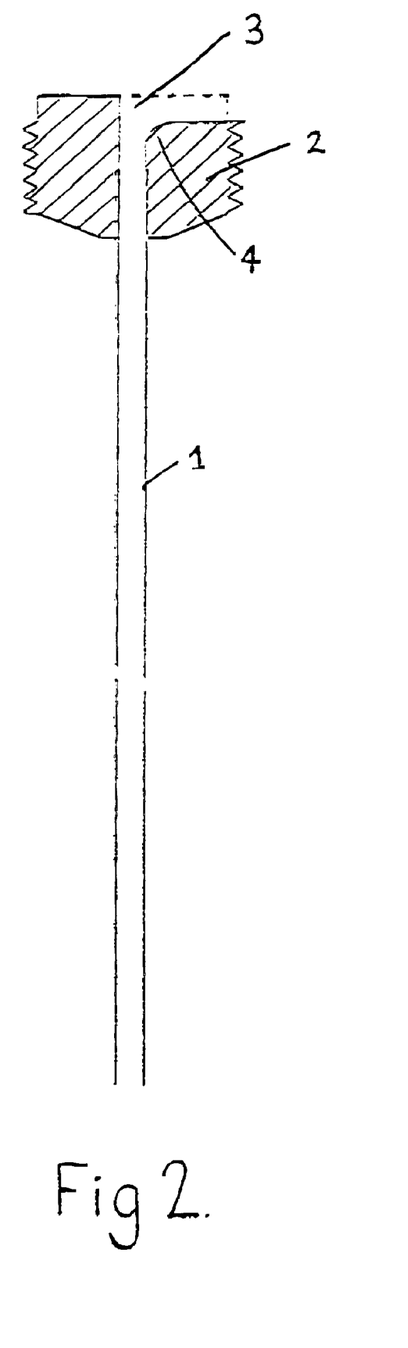
FIG. 2 Shows in cross section a guide device.
Figure 3:
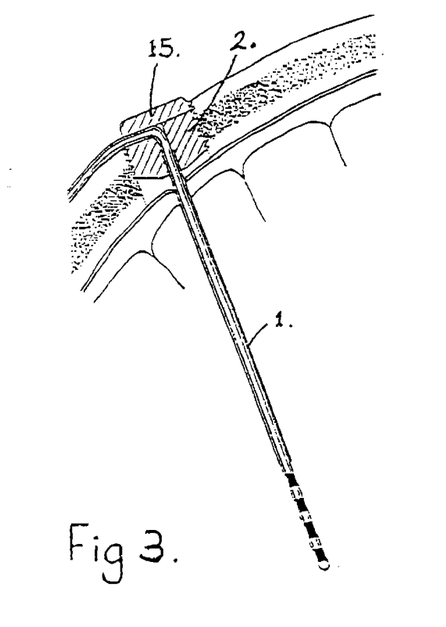
FIG. 3 Shows in a cross section a guide device fixed in a pre-tapped drill hole formed in a skull of a patient. A DBS electrode is inserted into the guide device.
Figure 6:
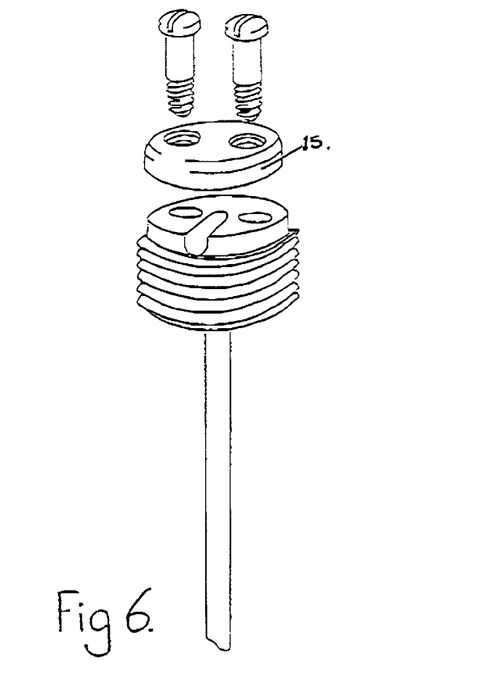
FIG. 6 Shows in perspective a cap which is screwed onto the head of the guide device and which fixes an instrument to the guide device.

FIGS. 1 and 2 show a guide device comprising a tube (1) that has a head attached to one end thereof. The head has a passageway therethrough in communication with the bore of the tube (1) and which terminates in an opening (3) on the outer surface of the head. The head has a screw thread formed on its external surface. The head of the guide device has a slot which extends laterally of the longitudinal axis of the tube (1) from the passageway to an outer surface of the head. The union (4) between the passageway of the head and the slot is radiussed such that any instrument inserted into the guide device can have its protruding end located within the slot (see FIG. 3). By having the union radiussed, the instrument is prevented from kinking when its protruding end is inserted into the slot. Two diametrically opposed drill holes are disposed of the outer surface of the head and run parallel to the longitudinal axis of the bore of the tube. These holes provide sockets (5) for engagement with a screwdriver (FIG. 6). The screwdriver has a cylindrical body (6) and projecting rods (7) that engage with the sockets (5) in the head. A radial slot (8) in the body of the screwdriver allows the screwdrivers rods to engage with the sockets in the guide tubes fixation means while the slot is being guided along an electrode or guide rod that is fixed at a desired trajectory by a stereo guide.

Prior to inserting the guide device, a drill hole is made in the skull along a desired trajectory. The drill is guided by a stereo guide and the drill hole is then tapped. An electrode or guide rod is now directed through the tapped hole and to the desired target. The tube of the guide device is cut to the desired length and is inserted over the electrode or guide rod and passed down the electrode or guide rod into the hole until the head of the guide device engages with the tapped hole in the skull. The screwdriver is now used to screw the head into the hole formed in the skull and the electrode or guide wire is removed.

In those circumstances in which the planned trajectory of the guide device is changed after drilling and tapping the skull, then, to accommodate the head of the guide device, the hole can be enlarged to form a burr hole and a small amount of acrylic cement placed extradurally in the burr hole. Then head is then seated in the acrylic cement which will set hard and secure the guide device to the skull in the desired trajectory (see FIG. 4). Engagement of the hardened acrylic cement with the screw tread formed on the head ensures that the guide device can be removed at a future date by unscrewing it. When the guide device has been inserted, typically a few millimeters short of the desired target, a plastic radio-opaque stylette (FIG. 4) may be cut to length (i.e. the distance from the top of the head of the guide device to the desired target site) and insert it to the guide device to allow radiological confirmation of its position (see FIG. 4).

Figure 4:
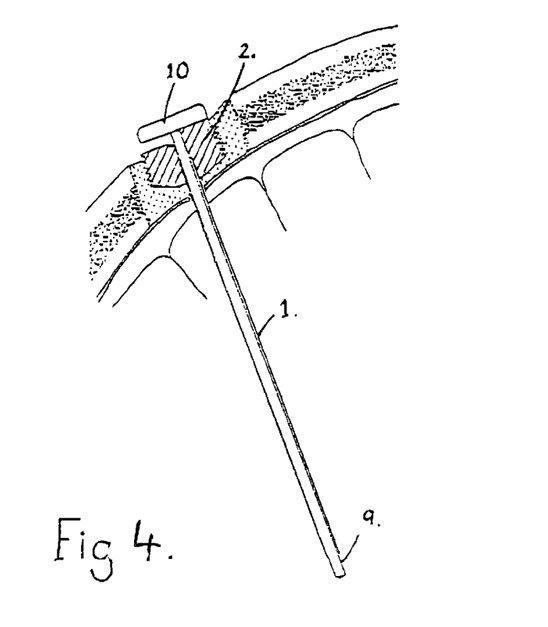
FIG. 4 Shows a cross section of the guide device fixed within a large diameter bur hole using an acrylic cement. A radio-opaque stylette is inserted into the guide device.
Figure 5:
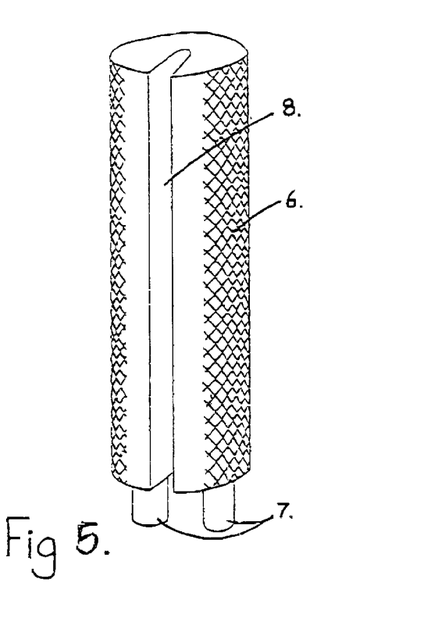
FIG. 5 Shows in perspective a screw-driver to insert the implantable guide tube.

The stylette comprises a plastic rod (9) with an external diameter just smaller than the internal diameter of the bore of the guide device. The plastic rod (9) is connected to a plastic disc (10) that acts as a stop and a cap, and engages with the outer surface of the head.

For staged or repeated lesioning at the target site the stylette is withdrawn and a stimulation/lesioning electrode is inserted to the same depth. The target site is stimulated or electrically depolarised to mimic a lesion and the electrode position is finally adjusted to achieve maximal functional benefit prior to creating a permanent radio-frequency lesion.

Figure 7:
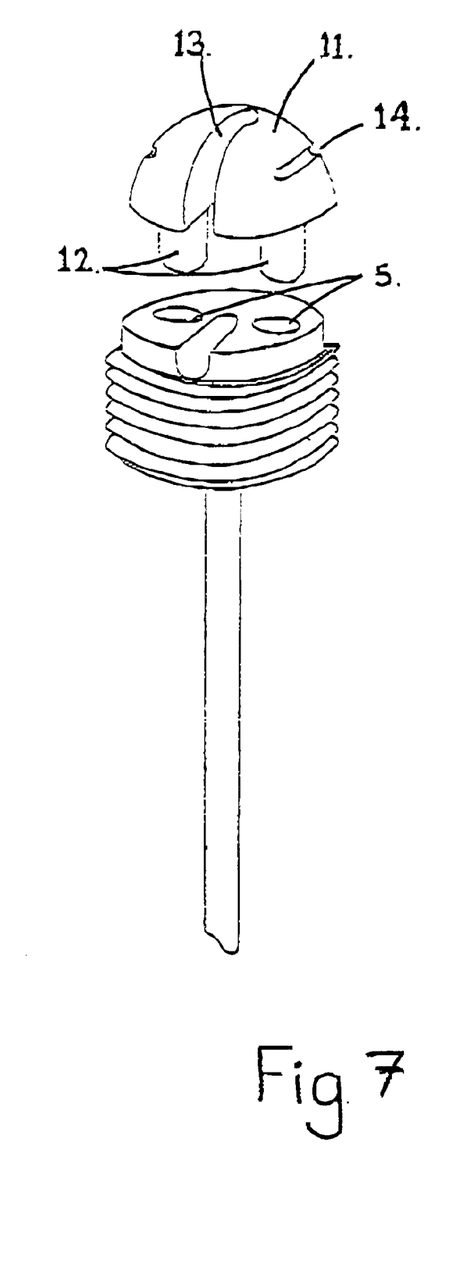
FIG. 7 Shows in perspective a dome attachable to the head of the guide device to assist in placement and fixation of an instrument within the guide device.

Deep brain stimulation (DBS) electrodes and catheters are flexible and are generally inserted into the brain on a guide wire. When the target is reached, the guide wire is removed and the end of the electrode or catheter protruding from the head is bent through about 90° and anchored relative to the skull surface prior to connection to a pulse generator or pump. This process may result in displacement of the catheter or electrode. To assist in this manoeuvre and prevent displacement an attachable dome (11) is preferably attached to the head of the guide device as shown in FIG. 7. The dome (11) has two projecting rods (12) which engage with sockets (5) in the head of the guide device. A slot (13) extends laterally from the central axis of the dome (11) to an outer surface of the dome. The slot (13) is sized to accommodate the electrode or catheter. Recesses (14) on the outer surface of the dome (11) provides points to hold and manipulate the dome (11) using forceps.

After inserting and fixing the guide device, and prior to introducing an electrode or catheter, the dome (11) is connected to the head of the guide device so that the rods (12) engage with the sockets (5). The distance of the desired target to the top of the dome (11) is measured and this distance equals the length of the catheter or electrode to be inserted.

Figure 8:
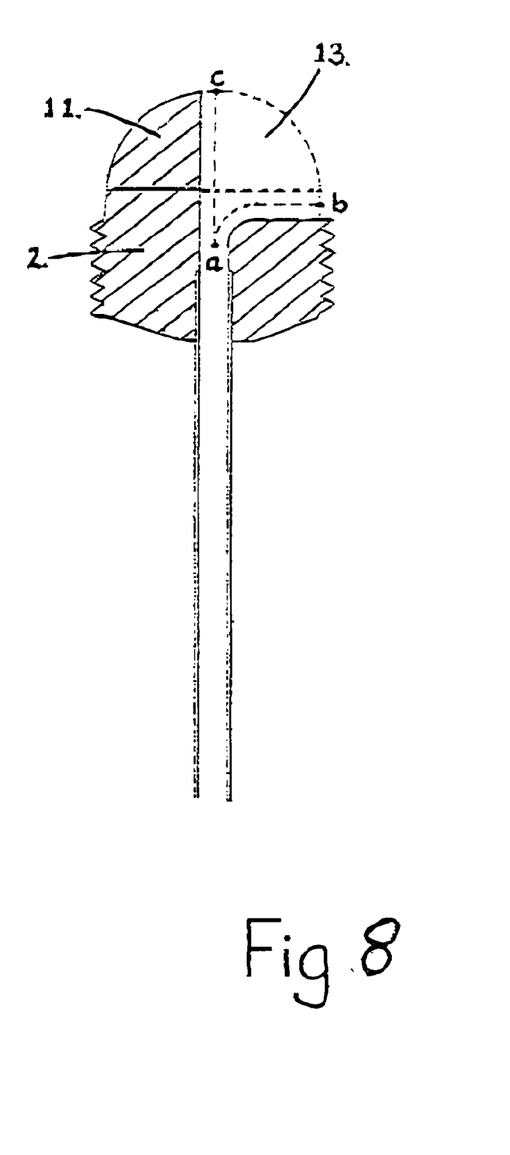
FIG. 8 Shows a cross section of a dome attached to the head of a guide device, wherein the distance ab=ac.

In FIG. 8, a cross section of the head of the guide device is shown wherein the dome (11) is attached. The distance a to b is equal to the distance a to c. Accordingly, if a stop formed on the electrode or catheter is kept in contact with the outer surface of the dome (11), when the protruding end of the electrode or catheter is bent through about 90° then the inserted end of the catheter or electrode will not be displaced from the target site during the manoeuvre. Once the electrode or catheter has been secured relative to the skull surface, then the dome (11) can be removed from the head.

The electrode or catheter may be directly fixed to the head of the guide device via a protective cap (is), (see FIG. 6). The protective cap (15) comprises a disc for which there are two diametrically opposed holes for screw fixation to the head of the guide device. On fixing the protective cap (15) to the head of the guide device, the under surface of the protective cap (15) comes into contact with the catheter or electrode as it lies in the slot and fixes the catheter or electrode in position. Alternatively, the protective cap (15) may be in the form of a disc with projecting rods that press fit into the holes (5) formed in the head of the guide device.

Figure 9:
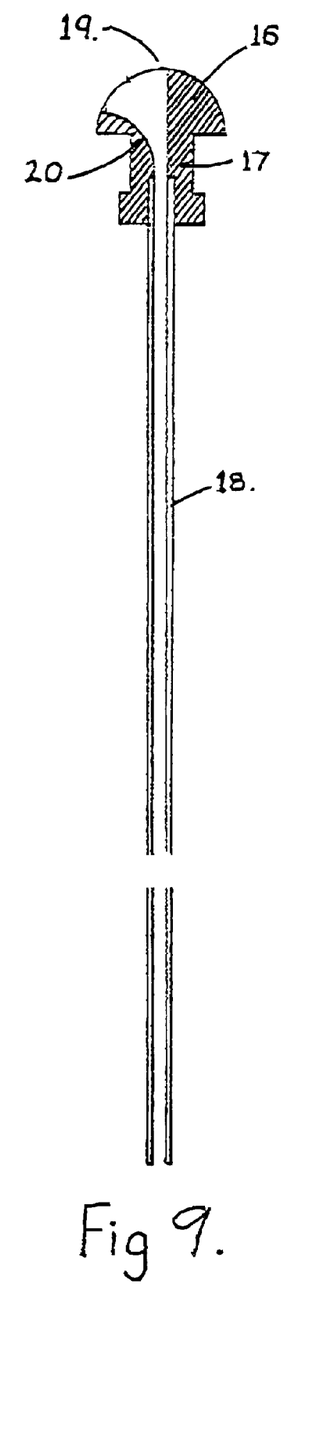
FIG. 9 Shows a cross section of a guide device.
Figure 10:
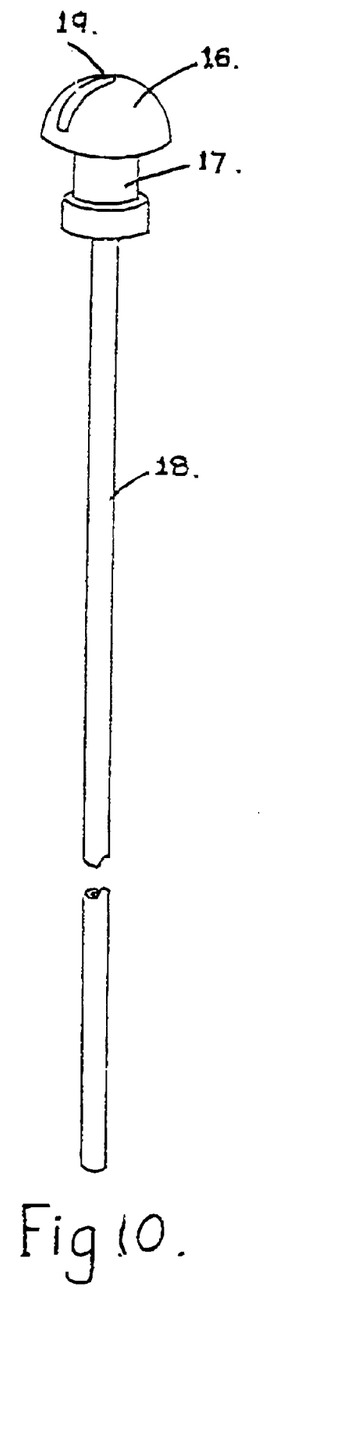
FIG. 10 Shows in perspective the guide device shown in FIG. 9.

A second embodiment of the guide device of the present invention is shown in FIGS. 9 and 10. In FIGS. 9 and 10, the head of the guide device has an opening (19) and a slot on a domed surface, wherein the dome (16) is intrical with the head. The head has a recess (17) which provides a surface for engagement with an acrylic cement for fixing it in the desire trajectory within a burr hole.

An electrode or catheter may be inserted on a guide wire through the opening (19) in the dome (16) and passed down through the bore of the tube (18) to the target site until a stop on the electrode or catheter contacts the outer surface of the dome (16). The guide wire is then withdrawn and the protruding end of the catheter or electrode is located within the slot formed in the head. During this maneuver, the stop is kept in contact with the outer surface of the dome (16) in order to prevent displacement of the inserted end of the electrode or catheter from the desired target.

Figure 11:
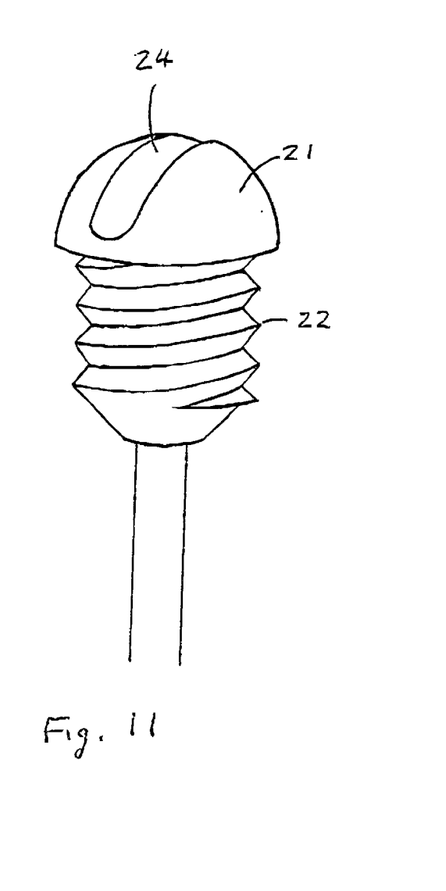
FIG. 11 Shows in perspective the head of a guide device.
Figure 12:
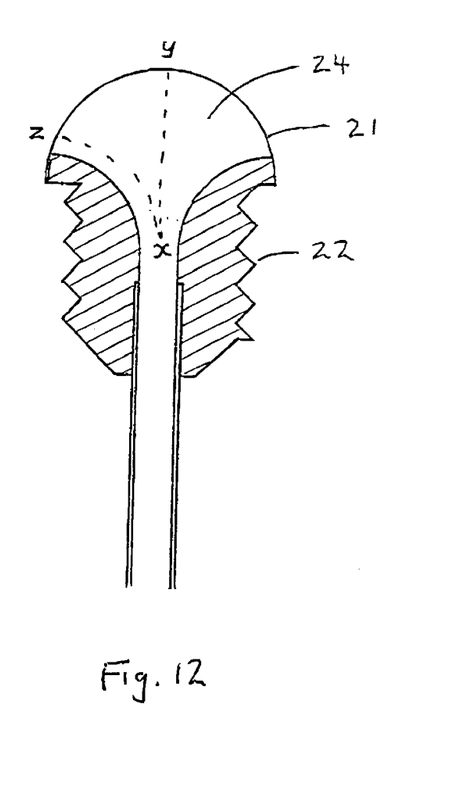
FIG. 12 Shows in cross section the head shown in FIG. 11.

A third embodiment of the head of the guide device of the present invention is shown in FIGS. 11 and 12. The head comprises a dome (21) and a thread (22) formed on the external surface of the head. When a guide device compressing the head is inserted, the thread (22) is screwed into a pretapped hole in the skull or is embedded in acrylic cement. A screwdriver may be used to remove the guide device by inserting the blade of a screwdriver into a slot (24) formed in the dome (21).

The head has a passageway in communication with the bore of the tube (23) connected to the head. The head of the guide device has a slot (24) which extends laterally from the longitudinal axis of the bore from the passageway to an outer surface of the dome (21). This slot (24) is created so that a protruding end of an electrode or catheter can be housed within the slot (24) enabling the protruding end to be bent through about 90°.

When a DBS electrode or catheter is inserted into the guide device comprising the head shown in FIGS. 11 and 12, it is preferable that a stop on the electrode or catheter is brought into contact with the outer surface of the dome (21). If this stop is kept in contact with the outer surface of the dome (21) when the protruding end of the catheter or electrode is bent through about 90°, the inserted end of the catheter or electrode will not move because the distance xy=xz (see FIG. 12).

What is claimed is:

1. A neurosurgical guide device comprising a tube for insertion into a brain of a patient to a vicinity of a desired target, wherein the tube has a head attached to one end thereof, the head having a passageway therethrough in communication with a bore of the tube and which terminates in an opening on the outer surface of the head, and having one or more formations on the head's external surface for securing the device in a hole formed in a skull of a patient, whereby an instrument can be introduced through the opening and passed along the bore from a proximal end to a distal end thereof.

2. The guide device of claim 1, wherein the one or more formations is a screw thread.

3. The guide device of claim 1, wherein the head has a slot which extends laterally of the longitudinal axis of the bore from the passageway to an outer surface of the bead, for receiving, in use, a protruding end of an instrument located in the device.

4. The guide device of claim 3, wherein the passageway from the bore to the slot is radiussed.

5. The guide device of claim 3, wherein the length of the path from the distal end of the bore to the opening on the head is substantially the same as the length of a path from the distal end of the bore to the outer surface end of the slot on the head.

6. The guide device of claim 5, wherein the opening of the head and the outer surface end of the slot are on a domed surface.

7. A method of positioning an instrument at a desired target in the brain of a patient, comprising:
    (a) drilling a hole in the skull of the patient along a desired trajectory;
    (b) inserting a neurosurgical guide device comprising a tube for insertion into a brain of a patient to a vicinity of a desired target, wherein the tube has a head attached to one end thereof, the head having a passageway therethrough in communication with the bore of the tube and which terminates in an opening on the outer surface of the head, and having one or more formations on its external surface for securing the device in a hole formed in a skull of a patient, into the hole along the desired trajectory and securing the head in the hole; and
    (c) inserting the instrument through the opening and passing the instrument along the bore so that the instrument is positioned at the desired target.

8. The method of claim 7, wherein the device is inserted by inserting a guide rod into the hole, inserting the device over the guide rod so that the guide rod is present within the bore of the device and moving the device along the guide rod until the device is at the desired position.

9. The method of claim 7, wherein a radio opaque stylette is removably inserted into the device in order to determine the position of the desired target.

10. The method of claim 9, wherein the stylette has a cap which seals the opening in the head of the device when the stylette is removably inserted into the device.

11. The method of claim 7, wherein the head is directly attached to the skull.

12. The method of claim 7, wherein the head is indirectly attached to the skull via a filler.

13. The method of claim 7, wherein the instrument has a stop which contacts an outer surface of the head and prevents further insertion of the instrument into the device.

14. The method of claim 7, wherein the the head of the device has a slot which extends laterally of the longitudinal axis of the bore from the passageway to an outer surface of the head, and wherein an end of the inserted instrument protrudes from the opening of the enlarged head and is located in the slot.

15. The method of claim 14, wherein the instrument has a stop which contacts an outer surface of the head and prevents further insertion of the instrument into the device, and the stop is kept in contact with the outer surface of the head while the protruding end of the instrument is located in the slot.

16. A kit for performing neurosurgery comprising:
    (a) a neurosurgical guide device comprising a tube for insertion into a brain of a patient to a vicinity of a desired target, wherein the tube has a head attached to one end thereof, the head having a passageway therethrough in communication with the bore of the tube and which terminates in an opening on the outer surface of the head, and having one or more formations on its external surface for securing the device in a hole formed in a skull of a patient, whereby an instrument can be introduced through the opening and passed along the bore from a proximal end to a distal end thereof;
    (b) an instrument for insertion into the device;
    (c) a drill bit for forming a hole in the skull to receive the device; and
    (d) a guide rod for guiding the device into the hole.

17. The kit of claim 16, which further comprises a radio opaque stylette for insertion into the device.

18. A neurosurgical guide device comprising a tube for insertion into a brain of a patient to a vicinity of a desired target, wherein the tube has a head attached to one end thereof, the head having a passageway therethrough in communication with the bore of the tube and which terminates in an opening on the outer surface of the head, and having one or more formations on its external surface for securing the device in a hole formed in a skull of a patient, whereby an instrument can be introduced through the opening and passed along the bore from a proximal end to a distal end thereof, and wherein the head has a slot which extends laterally of the longitudinal axis of the bore from the passageway to an outer surface of the head, for receiving, in use, a protruding end of an instrument located in the device.

19. A device according to claim 1, the distal end of the core being open.

* * * * *

UNITED STATES PATENT AND TRADEMARK OFFICE
CERTIFICATE OF CORRECTION

PATENT NO. : 6,609,020 B2  Page 1 of 1
DATED : August 19, 2003
INVENTOR(S) : Steven Gill It is certified that error appears in the above-identified patent and that said Letters Patent is hereby corrected as shown below:

Column 1,
Line 57, please delete "teed-back", and insert therefor -- feed-back --.

Column 3,
Line 25, after "length", please insert therefor -- . -- (period).
Line 51, please delete "device,", and insert therefor -- device. --.

Column 10,
Line 22, please delete "(is)", and insert therefor -- (15) --.

Column 11,
Line 24, please delete "bead", and insert therefor -- head --.

Column 12,
Line 57, please delete "core", and insert therefor -- bore --.

Signed and Sealed this

Tenth Day of February, 2004

JON W. DUDAS
*Acting Director of the United States Patent and Trademark Office*